United States Patent
Chen

(10) Patent No.: US 9,602,584 B2
(45) Date of Patent: Mar. 21, 2017

(54) SYSTEM WITH DISTRIBUTED PROCESS UNIT

(71) Applicant: Gemtek Technology Co., Ltd., Hsinchu (TW)

(72) Inventor: Hung Wen Chen, Zhubei (TW)

(73) Assignee: Gemtek Technology Co., Ltd., Hsinchu (TW)

( * ) Notice: Subject to any disclaimer, the term of this patent is extended or adjusted under 35 U.S.C. 154(b) by 231 days.

(21) Appl. No.: 14/229,500

(22) Filed: Mar. 28, 2014

(65) Prior Publication Data

US 2014/0304317 A1 Oct. 9, 2014

(30) Foreign Application Priority Data

Mar. 29, 2013 (CN) ...................... 2013 2 0155258 U
May 31, 2013 (CN) .......................... 2013 1 0214981
Jul. 4, 2013 (CN) .......................... 2013 1 0279676

(51) Int. Cl.
*H04L 29/08* (2006.01)
*H04W 4/00* (2009.01)
*A61B 5/00* (2006.01)

(52) U.S. Cl.
CPC ............ *H04L 67/10* (2013.01); *A61B 5/0015* (2013.01); *H04W 4/008* (2013.01)

(58) Field of Classification Search
CPC ............................... H04L 67/10; H04W 4/008
USPC ........................................................ 709/201
See application file for complete search history.

(56) References Cited

U.S. PATENT DOCUMENTS

| | | | | |
|---|---|---|---|---|
| 2006/0132382 A1* | 6/2006 | Jannard | .................. | G02C 11/06 345/8 |
| 2013/0311540 A1* | 11/2013 | Fyke | ..................... | H04L 67/125 709/201 |
| 2013/0326790 A1* | 12/2013 | Cauwels | ............. | A44C 5/2071 2/170 |
| 2013/0335671 A1* | 12/2013 | Fleck | ................... | G02B 27/017 349/62 |
| 2014/0101755 A1* | 4/2014 | Tang | ....................... | G06F 21/35 726/20 |

* cited by examiner

*Primary Examiner* — Suraj Joshi
(74) *Attorney, Agent, or Firm* — Winston Hsu; Scott Margo

(57) ABSTRACT

The present invention provides a system with a separate computing unit, comprising: a primary computing device comprising a computing unit, a control interface unit via which a user enters an instruction that causes the computing unit to perform the processing operation or the computing operation to generate an instruction code, and a first wireless communication unit transmitting a first wireless signal containing the instruction code; and a remote control device comprising an instruction implementation unit, and a second wireless communication unit receiving the first wireless signal and sending the instruction code in the first wireless signal to the instruction implementation unit to implement the instruction code; wherein the operation of the instruction implementation unit of the remote control device is controlled by the instruction code.

12 Claims, 6 Drawing Sheets

SYSTEM WITH DISTRIBUTED PROCESS UNIT

CROSS-REFERENCE TO RELATED APPLICATIONS

This non-provisional application claims priority under 35 U.S.C. §119(a) on Patent Application No(s). CN201320155258.X filed in China on Mar. 29, 2013, CN201310214981.5 filed in China on May 31, 2013, and CN201310279676.4 filed in China on Jul. 4, 2013, the entire contents of which are hereby incorporated by reference.

BACKGROUND OF THE INVENTION

Field of the Invention

The present invention relates to a separate computing system, and more particularly, to a wireless communication system with a separate computing unit.

Description of the Prior Art

Due to technological advancement, wearable electronic apparatuses are becoming more popular with consumers and come in a wide variety of categories and functionalities. In this regard, users expect wearable electronic apparatuses, such as a pair of eyeglasses capable of projecting images or a wristband capable of detecting a pulse, to have excellent electronic computation functionality while maintaining minimized weight and low power consumption.

Minimized weight and low power consumption, however, are usually secured at the expense of electronic computation functionality because a high-performance processor, which is prerequisite to excellent computation functionality, inevitably consumes much power or causes heat dissipation problem.

Accordingly, how to reduce the weight and power consumption and increase the heat dissipation efficiency of a wearable electronic apparatus is an imperative issue to be addressed.

SUMMARY OF THE INVENTION

In view of the aforesaid drawbacks of the prior art, the present invention involves transmitting, via wireless transmission, the data to be computed from a wearable electronic apparatuses to a high-performance processor equipped in a mobile communication device, such as a smartphone, a tablet computer, or a hand-held game console, or to a microcomputer equipped with a separate computing processor, to undergo the processing and computing operations. Upon completion of the computing operation, the result can be selectively returned or not returned, depending on the situation. Alternatively, the user can directly enter an instruction to a mobile communication device or a microprocessor to perform the computing and processing operations with a processor or microprocessor of the mobile communication device, and then the result of the computing and processing operations is transmitted, via a wireless transmission unit, to the electronic apparatuses. In fact, a processor or microprocessor of an existing mobile device, such as a smartphone, not only features a high computation clock rate but also has multiple cores for executing program instructions separately and independently, thereby increasing the speed of program execution with the multiplexing of parallel computing.

According to an object of the present invention, there is provided a system with a separate computing unit, comprising: a primary computing device comprising a computing unit, a control interface unit via which a user enters an instruction that causes the computing unit to perform the processing operation or computing operation to generate an instruction code, and a first wireless communication unit transmitting a first wireless signal containing the instruction code; and a remote control device comprising an instruction implementation unit, and a second wireless communication unit receiving the first wireless signal and sending the instruction code in the first wireless signal to the instruction implementation unit to implement the instruction code; wherein the operation of the instruction implementation unit of the remote control device is controlled by the instruction code.

According to the above conception, the control interface unit is selected from one of a touchscreen, a voice-controlled device, and a physical key. Each of the first wireless communication unit and the second wireless communication unit is selected from one of a WiFi communication unit, an NFC communication unit, a RFID communication unit, a Bluetooth communication unit, a Zigbee communication unit, and an infrared communication unit.

According to the above conception, it is preferable that the instruction is an uncoded control signal, and the value of a register of the instruction implementation unit is changed according to the control signal so as to control the instruction implementation unit to perform a specific operation.

According to the above conception, the second wireless communication unit of the remote control device transmits a second wireless signal, the first wireless communication unit of the primary computing device receives and sends the second wireless signal to the computing unit to processing operation or advanced computing operation, and the control interface unit displays the result of the advanced processing operation or advanced computing operation.

According to the above conception, the second wireless communication unit of the remote control device transmits a second wireless signal, the first wireless communication unit of the primary computing device receives and sends the second wireless signal to the computing unit to perform advanced processing operation or advanced computing operation, and the result of the advanced processing operation or advanced computing operation is sent to the second wireless communication unit by the first wireless communication unit, thereby causing the instruction implementation unit to implement or display the result.

According to the above conception, it is preferable that the remote control device further has a microprocessor that processes the instruction code and controls the instruction implementation unit. Preferably, the remote control device is a pair of eyeglasses equipped with a projection element via which an image is projected onto a lens, and the content of the image is determined after the microprocessor has processed the instruction code. The pair of eyeglasses further has an eyeball detection device that transmits, via the second wireless communication unit, a second wireless signal after detecting a current position of the user's eyeballs, and the first wireless communication unit of the primary computing device receives and sends the second wireless signal to the computing unit to perform advanced processing operation and advanced computing operation.

According to the above conception, it is preferable that the remote control device is a watch that displays a piece of information on a screen thereof, and the content of the piece of information is determined after the microprocessor has processed the instruction code. The watch further has a detection device that transmits, via the second wireless communication unit, a second wireless signal after detecting the user's physiological information, and the first wireless communication unit of the primary computing device receives and sends the second wireless signal to the computing unit to perform advanced processing operation or advanced computing operation. The physiological information is selected from the information relating to the user's blood pressure, pulse, voice, and vibration.

In another embodiment, it is preferable that the instruction implementation unit of the remote control device is a screen that displays an information frame, and the content of the information frame is determined after the microprocessor has processed the instruction code. Alternatively, the instruction implementation unit of the remote control device is an input device that provides an input interface for the user to enter an advanced instruction, and the second wireless communication unit transmits a second wireless signal containing the advanced instruction. Next, the first wireless communication unit of the primary computing device receives and sends the second wireless signal to the computing unit to perform advanced processing operation or advanced computing operation. The input device is one of a keyboard, a mouse, a microphone, a camcorder, and a touchscreen, or a combination thereof. The input device is preferably synchronized by means of the computing unit of the primary computing device first, and then receives and displays the entered instruction on another remote control device's screen or the control interface unit.

According to the above conception, the primary computing device further comprises an identity authentication unit configured to perform an identity authentication procedure on the remote control device. The system of the present invention further comprises one or more other remote control devices synchronously controlled by the primary computing device through the first wireless signal.

With the aforementioned arrangement a wearable electronic apparatus requires either no processor at all or only a simple microprocessor because all the complicated computing operations are performed on a mobile communication device, such as a smartphone, or a microcomputer with a separate processor by means of wireless transmission, thereby fulfilling the goals of minimized weight, low power consumption, reduced cost, and enhanced computing capability.

DETAILED DESCRIPTION OF THE EMBODIMENTS

Figure 1:
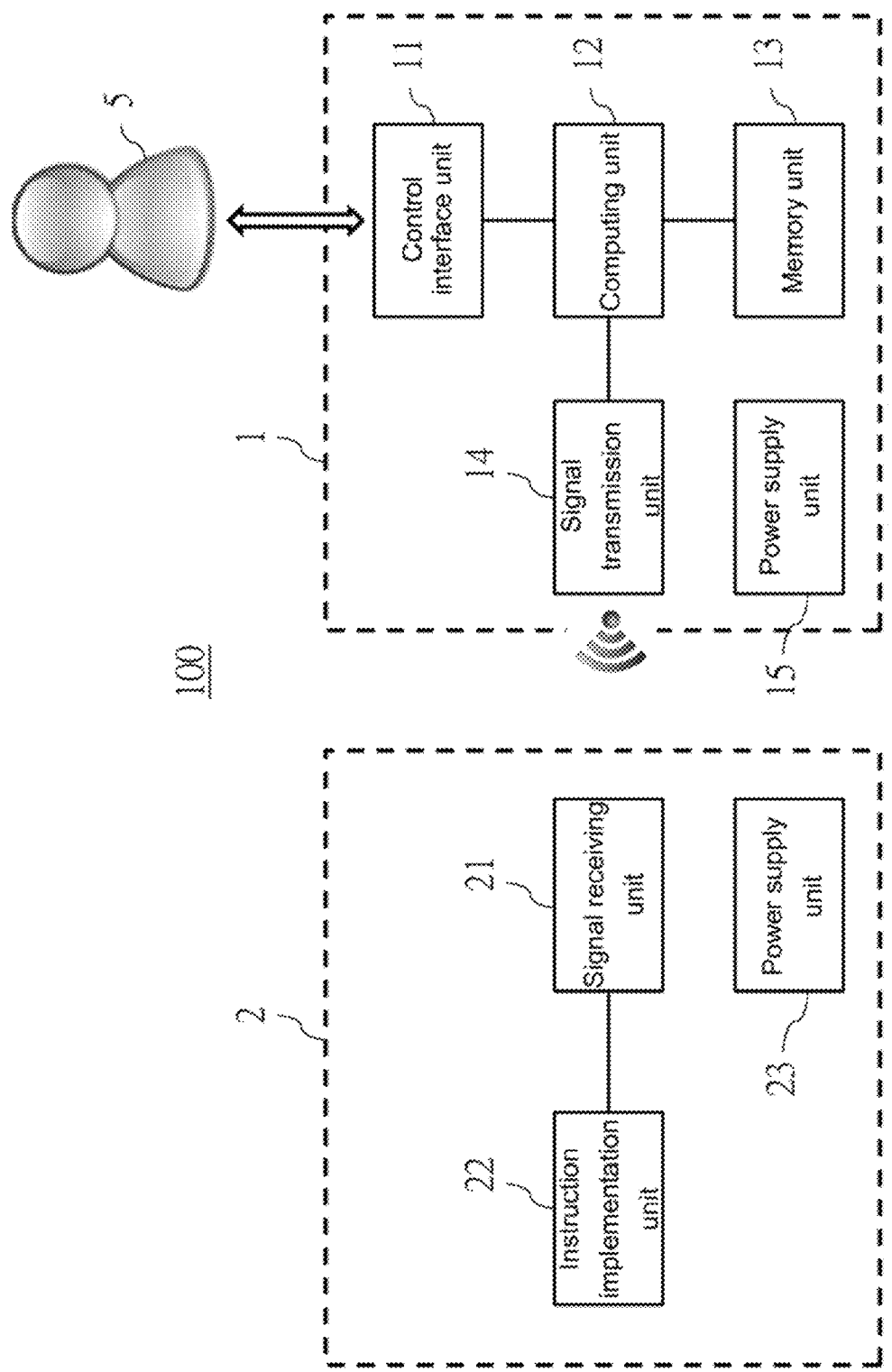
FIG. 1 is a block diagram illustrating the function of a separate computing system according to the first embodiment of the present invention.

The present invention will be described more fully hereinafter with specific embodiments by reference to the accompanying drawings. Reference numerals used herein refer to those shown in the drawings. When used herein, the words "comprise", "comprises", and "comprising" are open-ended terms and shall be construed as "include, without limitation", "includes, without limitation", and "including, without limitation", respectively. Moreover, a person having ordinary knowledge in the art understands that the same component/product may have a number of different names. For instance, the terms "processor" and "computing unit" refer to the same thing. Hence, components/products belonging to the same technical field as the present invention and having functions similar to those described herein fall within the scope of the present invention.

Referring to FIG. 1, there is shown a block diagram illustrating the function of a separate computing system according to the first embodiment of the present invention. As shown in FIG. 1, there is a separate computing system 100 of the present invention, comprising: a primary computing device 1 comprising a control interface unit 11, a computing unit 12, a memory unit 13, a signal transmission unit 14, and a power supply unit 15; and a remote control device 2 comprising a signal receiving unit 21, an instruction implementation unit 22, and a power supply unit 23.

The control interface unit 11 of the primary computing device 1 has an operation interface via which a user 5 can control the operation of the primary computing device 1. Preferably, the control interface unit 11 is selected from one of a touchscreen, a voice-controlled device, and a physical key. The computing unit 12 refers generally to a logical computing device capable of executing complex computer programs, such as an integrated circuit central processing unit or a microprocessor. The computing unit 12 can have one or more cores and is preferably capable of parallel computing or synchronous multithreaded computing. The memory unit 13 includes a volatile memory and/or a non-volatile memory and is configured to store the data of the primary computing device 1. The signal transmission unit 14 is configured to transmit externally messages from the primary computing device 1. The signal transmission unit 14 is selected from one of a WiFi communication unit, an NFC communication unit, a RFID communication unit, a Bluetooth communication unit, a Zigbee communication unit, and an infrared communication unit. The power supply unit 15, which can be, for example, one of a lead-acid battery, a nickel-cadmium battery, a nickel-hydride battery and a lithium ion battery, is configured to supply power to all electronic components in the primary computing device 1.

The signal receiving unit 21 of the remote control device 2 is configured to receive external wireless signals and to send the received wireless signals to the instruction implementation unit 22 to perform certain specific operations. The signal receiving unit 21 of the remote control device 2 is selected from one of a WiFi communication unit, an NFC communication unit, a RFID communication unit, a Bluetooth communication unit, a Zigbee communication unit, and an infrared communication unit. The power supply unit 23 of the remote control device 2, which can be, for example, one of a lead-acid battery, a nickel-cadmium battery, a nickel-hydride battery and a lithium ion battery, is configured to supply power to all electronic components in the remote control device 2.

Figure 2:
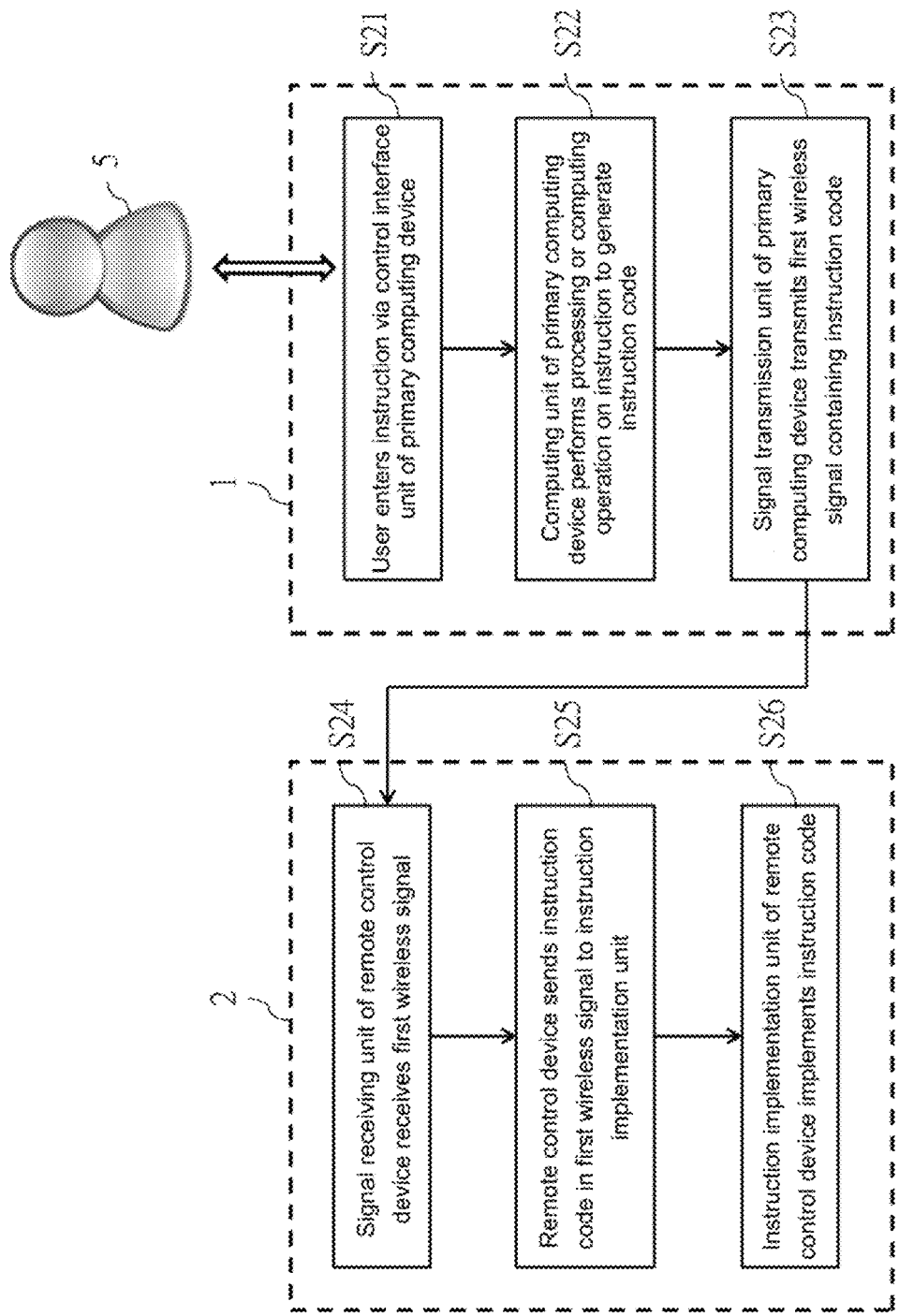
FIG. 2 is a flow chart illustrating the operation of the separate computing system according to the first embodiment of the present invention.

Referring to FIG. 2, there is shown a flow chart illustrating the operation of the separate computing system according to the first embodiment of the present invention. As shown in FIG. 2, steps S21~S23 are implemented on the primary computing device 1, and steps S24~S26 are implemented on the remote control device 2. For the sake of better understanding of the present invention, the primary computing device 1 is exemplified by a smartphone, and the remote control device 2 is exemplified by a wristband with an LED light-emitting unit and a wireless signal receiver. However, a person having ordinary knowledge in the art understands that the primary computing device 1 can also be one of other mobile communication devices, such as a tablet computer, a notebook computer, a hand-held game console, and a multimedia player, or a microcomputer having independent processing and computing capability, and that the remote control device 2 can be a wearable device with a wireless signal receiver, such as a watch, a pair of eyeglasses, or a headset, or a remotely controlled device capable of being synchronized. The first embodiment described herein is to be deemed as illustrative, rather than restrictive, of the scope of the present invention.

In step S21, the user enters an instruction through a touchscreen (i.e., the control interface unit 11) of the smartphone (i.e., the primary computing device 1 shown in FIG. 1.) For instance, the instruction demands that the smartphone transmit a wireless signal to a wristband with an LED light-emitting unit and a wireless signal receiver (i.e., the remote control device 2) according to the current temperature or rainfall.

In step S22, after receiving the instruction, a central processing unit (i.e., the computing unit 12) of the smartphone performs the processing and computing operations so as to, for example, obtain information about the current temperature or rainfall and determine the light-emitting state of the LED light-emitting unit according to the current temperature or rainfall. In step S23, the central processing unit of the smartphone instructs the signal transmission unit 14 to transmit a first wireless signal containing an instruction code after making the determination. The instruction code is preferably an uncoded control signal. Furthermore, the first wireless signal complies with WiFi communication protocol, NFC communication protocol, RFID communication protocol, Bluetooth communication protocol, or Zigbee communication protocol.

In step S24, a wristband with an LED light-emitting unit and a wireless signal receiver (i.e., the remote control device 2) receives, via the signal receiving unit 21, the first wireless signal. In step S25, the wristband (i.e., the remote control device 2) sends the instruction code in the first wireless signal to the LED light-emitting unit (i.e., the instruction implementation unit 22). In step S26, the wristband changes the value of the LED light-emitting unit's control register according to a control signal of the instruction code so as to control the indicator status.

Therefore, a user wearing the wristband knows the current temperature or rainfall according to the LED indicator status. The present invention is advantageous in that the wristband, instead of being equipped with components of high power consumption and great weight, such as a processor or an input interface, exploits the screen and the central processing unit of the smartphone to manipulate the settings and perform the computing operation, thereby fulfilling the goals of reduced size, minimized weight, and low power consumption. Furthermore, the signal receiving unit 21 of the wristband requires no two-way communication capability but the capability of receiving signals, hence it is simpler in structure and consumes less power than a wireless communication unit capable of two-way communication.

Figure 3:
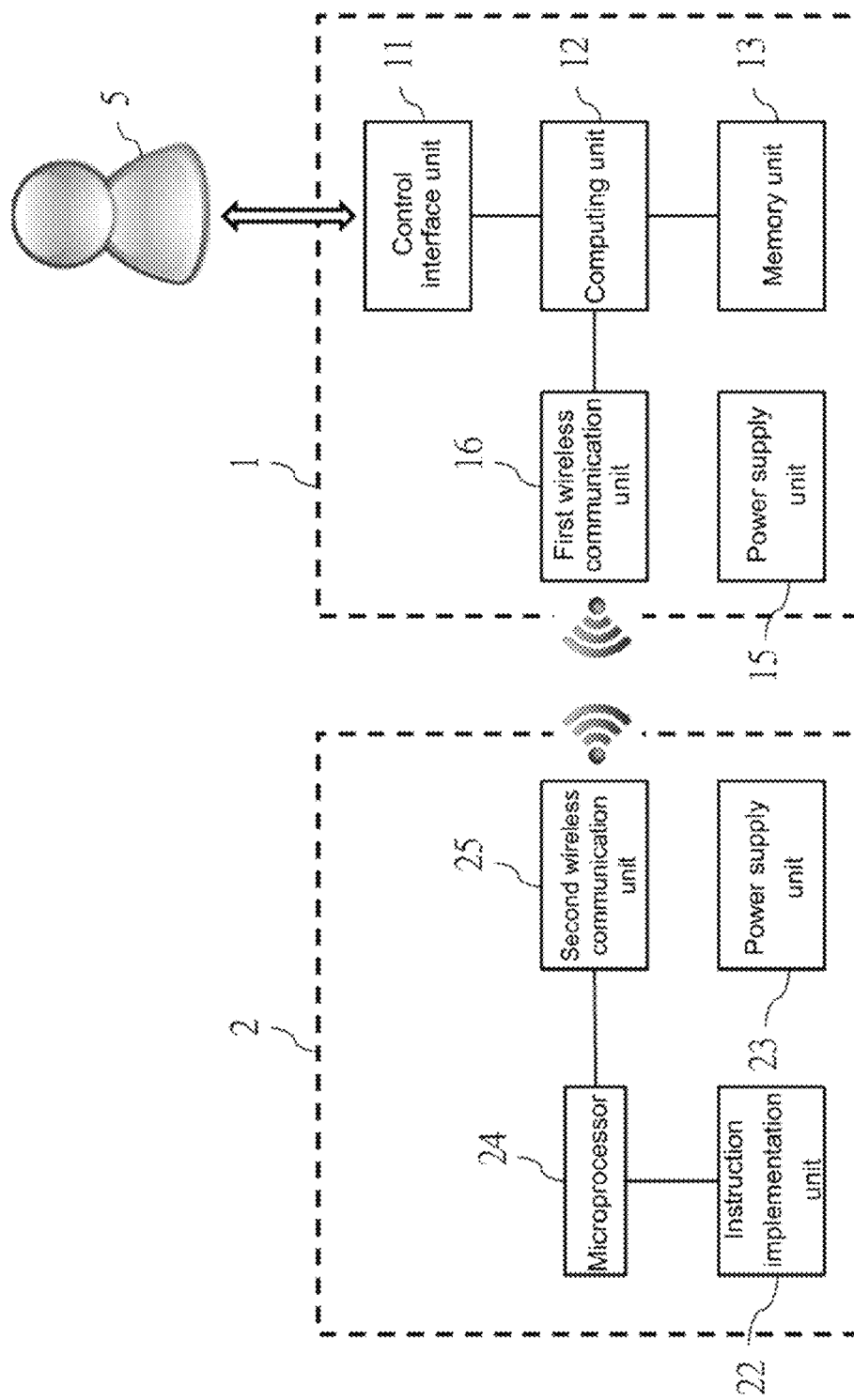
FIG. 3 is a block diagram illustrating the function of a separate computing system according to the second embodiment of the present invention.

Referring to FIG. 3, there is shown a block diagram illustrating the function of a separate computing system according to the second embodiment of the present invention. FIG. 3 is different from FIG. 1 in that the remote control device 2 further has a microprocessor 24 that processes an instruction code and controls the instruction implementation unit 22 to perform a specific operation. Although the remote control device 2 further has the microprocessor 24, the microprocessor 24 is merely used to control the instruction implementation unit 22, a second wireless communication unit 25, or any other detection device to perform sophisticated functions, rather than being used to perform general-purpose processing and computing tasks as the computing unit 12 of the primary computing device 1 does.

Figure 4:
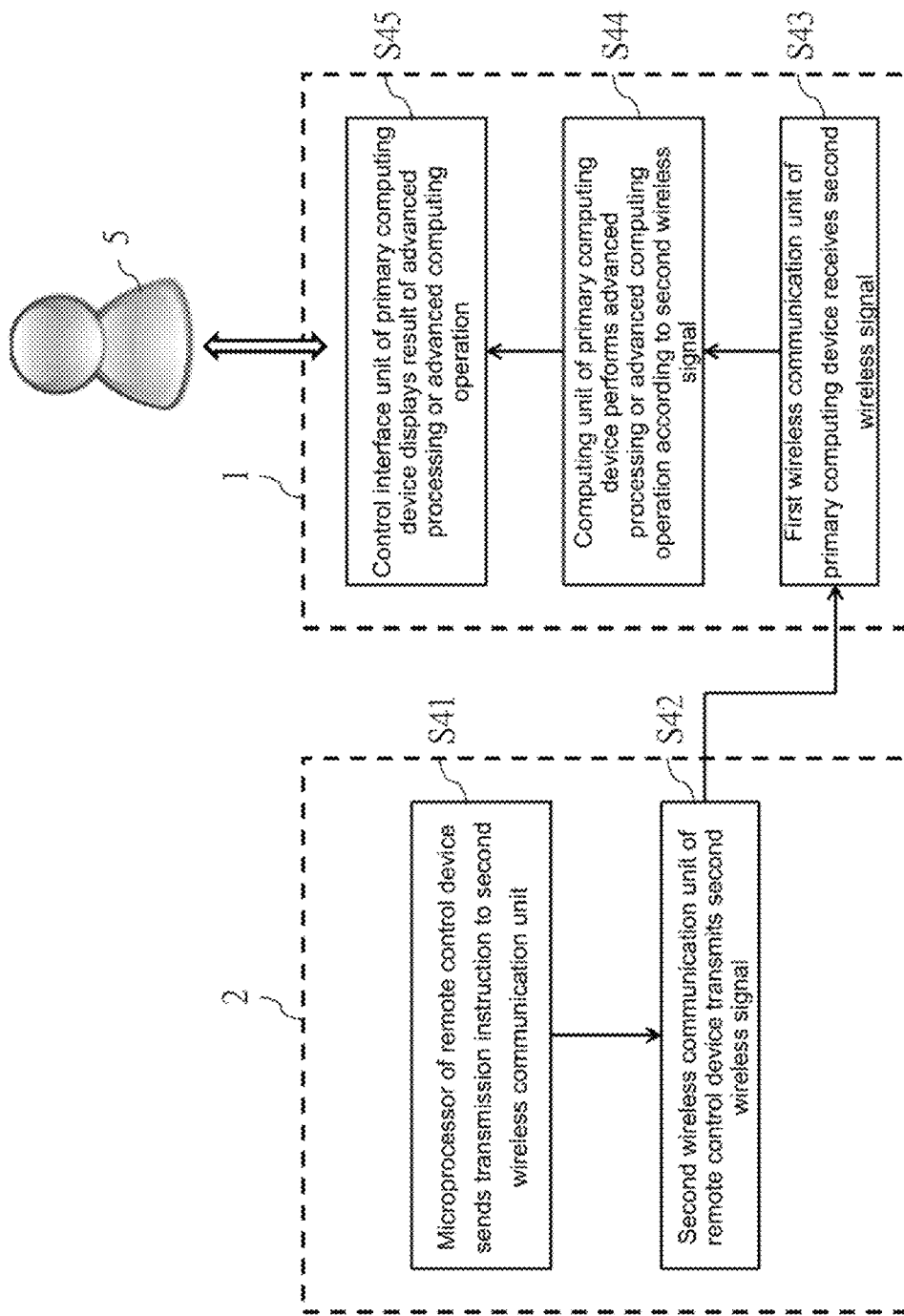
FIG. 4 is a flow chart illustrating the operation of the separate computing system according to the second embodiment of the present invention.

Referring to FIG. 4, there is shown a flow chart illustrating the operation of the separate computing system according to the second embodiment of the present invention. As shown in FIG. 4, steps S41~S42 are implemented on the remote control device 2, and steps S43~S45 are implemented on the primary computing device 1. For the sake of better understanding of the present invention, the primary computing device 1 is exemplified by a smartphone, and the remote control device 2 is exemplified by a watch and a pair of eyeglasses with a projection element. Similarly, the second embodiment described herein is to be deemed as illustrative, rather than restrictive, of the scope of the present invention. The flow chart in FIG. 4 omits, for example, the following similar operation processes depicted in FIG. 2: the smartphone transmits externally a generated instruction code by means of the first wireless communication unit after performing the processing operation or computing operation with the computing unit 12 according to the user's instruction; after the second wireless communication unit of the watch or the pair of eyeglasses with a projection element has received the instruction code, the microprocessor determines the content of a piece of information and displays it on the screen of the watch, or projects it onto the lenses of the pair of eyeglasses, according to the instruction code. For instance, with a smartphone and the aforesaid processes, a user can send the content of an email to a watch or a pair of eyeglasses with a projection element via wireless transmission, and then the content of the email is displayed on the screen of the watch or projected onto the lenses of the pair of eyeglasses.

In step S41, the microprocessor 24 of a watch or a pair of eyeglasses with a projection element (i.e., the remote control device 2) sends a transmission instruction to the second wireless communication unit 25. Next, in step S42, the second wireless communication unit 25 of the watch or the pair of eyeglasses with a projection element transmits externally a second wireless signal. For instance, the watch further has a detection device configured to detect physiological information pertaining to the user's blood pressure, pulse, voice, and vibration. Upon completion of the detection operation performed by the detection device, the microprocessor 24 of the watch transmits a transmission instruction to the second wireless communication unit 25 via which the physiological information is encapsulated in a second wireless signal and transmitted externally. In another example, the pair of eyeglasses with a projection element further has an eyeball detection device configured to detect a current position of the user's eyeballs and then transmit, via the second wireless communication unit 25, a second wireless signal. Unlike the signal receiving unit 21 in the first embodiment, the second wireless communication unit 25 in the second embodiment is capable of two-way (receiving-and-transmitting) wireless communication.

In step S43, a first wireless communication unit 16 of the smartphone receives the second wireless signal. In step S44, the computing unit 12 of the smartphone performs advanced processing operation or advanced computing operation according to the second wireless signal so as to, for example, calculate whether or not the physiological information relating to blood pressure, pulse, etc, measured by the watch falls within the normal range, perform voice recognition on voices, or record and convert vibration into burned calories. Alternatively, after the current position of the user's eyeballs measured by the pair of eyeglasses has been obtained, the computing unit 12 of the smartphone performs the computing operation according to the position and retrieves from the memory unit 13 or a cloud database information relating to a specific venue/shop in the direction of the user's eyeballs. In step S45, after the computing unit 12 of the smartphone has performed the advanced computing and processing operations, the control interface unit 11 displays the result of the advanced processing operation or advanced computing operation, such as the determination as to whether the blood pressure and pulse are normal, the result of voice recognition, the amount of burned calories, and information relating to a specific venue/shop in the direction of the user's eyeballs. Furthermore, the aforesaid results can also be sent back to the watch or the pair of eyeglasses with a projection element (i.e., the remote control device 2) via the first wireless communication unit 16 and displayed on the screen of the watch or projected onto the lenses of the pair of eyeglasses.

As can be seen from the above embodiment, certain information, after being obtained by the remote control device 2, can be sent to the primary computing device 1 to undergo advanced processing operation performed by the computing unit 12 of the primary computing device 1, and then the result of the processing operation is displayed on the screen of the primary computing device 1 or sent back to the remote control device 2 to be displayed. With such arrangement, the remote control device 2 is exempted from complicated processing or computing operations, and thus the number of essential components thereof can be minimized, thereby fulfilling the goal of minimized weight.

Although the aforesaid embodiment describes the transmission of physiological signal detected by a watch or a pair of eyeglasses to a smartphone, a watch or a pair of eyeglasses in another application can send, without limitation to physiological information, a wireless signal communicating the need to perform complicated computing operations to the smartphone to cause the computing unit 12 of the smartphone to perform such operations and send back the result. Therefore, the microprocessor 24 of the watch or the pair of eyeglasses does not require a powerful computation capability and its power consumption can be reduced significantly.

Figure 5:
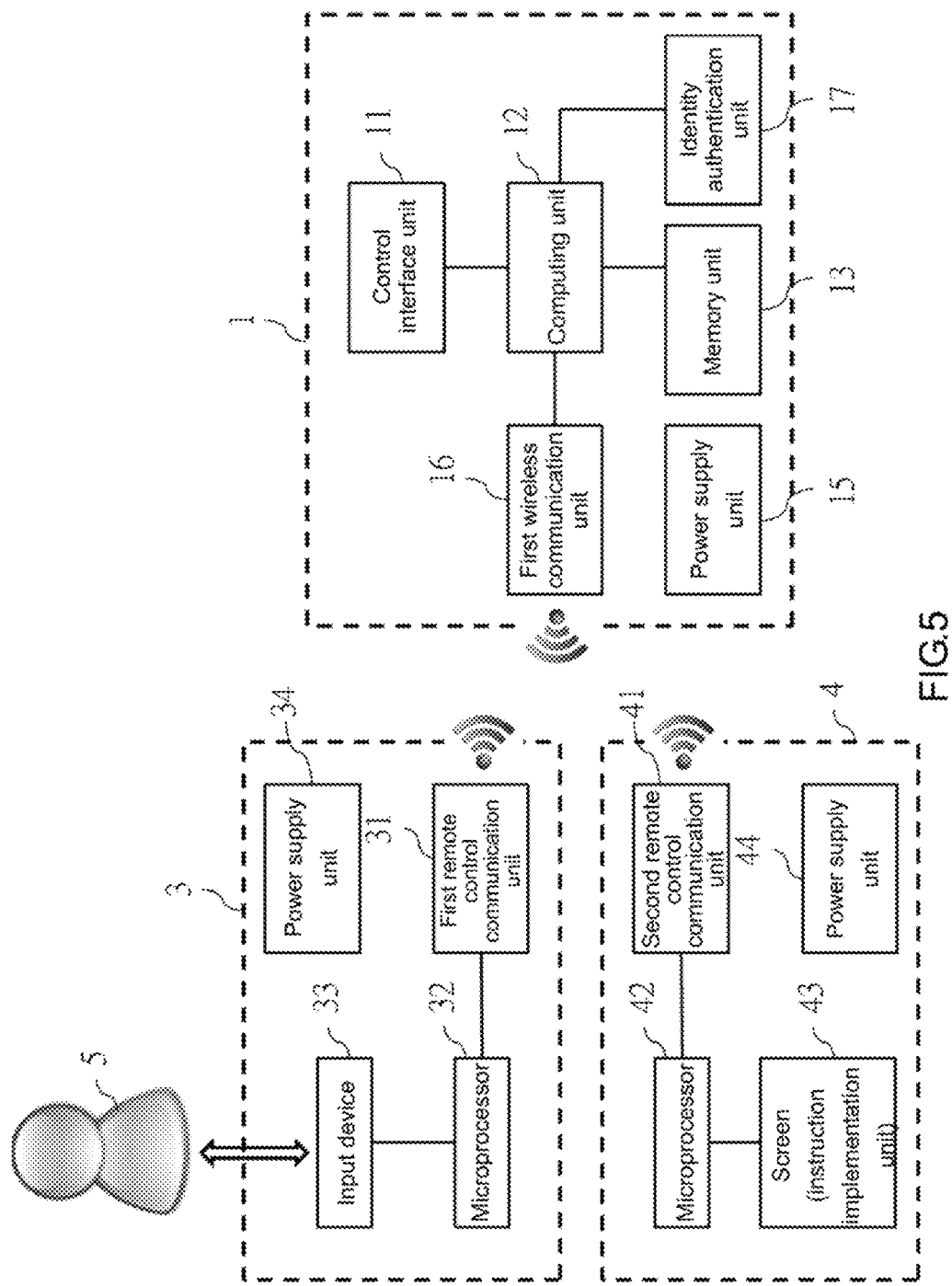
FIG. 5 is a block diagram illustrating the function of a separate computing system according to the third embodiment of the present invention.

Referring to FIG. 5, there is shown a block diagram illustrating the function of a separate computing system according to the third embodiment of the present invention. A first remote control device 3 has an input device 33 configured to provide an input interface for the user to enter an advanced instruction, and a first remote control communication unit 31 transmits a second wireless signal containing the advanced instruction; a first wireless communication unit 16 of a primary computing device 1 receives and sends the second wireless signal to a computing unit 12 to perform advanced processing operation or advanced computing operation; a second remote control device 4 has a screen 43 displaying an information frame whose content is determined after a microprocessor 42 has processed an instruction code. Furthermore, FIG. 5 is different from FIGS. 1 and 3 in that the primary computing device 1 is capable of synchronously controlling multiple remote control devices (exemplified by the first remote control device 3 and the second remote control device 4) via the first wireless communication unit 16, and that the primary computing device 1 further comprises an identity authentication unit 17 configured to perform an identity authentication procedure on the remote control devices 3 and 4. In practice, the identity authentication unit 17 performs the identity authentication procedure according to media access control addresses (also known as MAC addresses) of the remote control devices 3 and 4.

Figure 6:
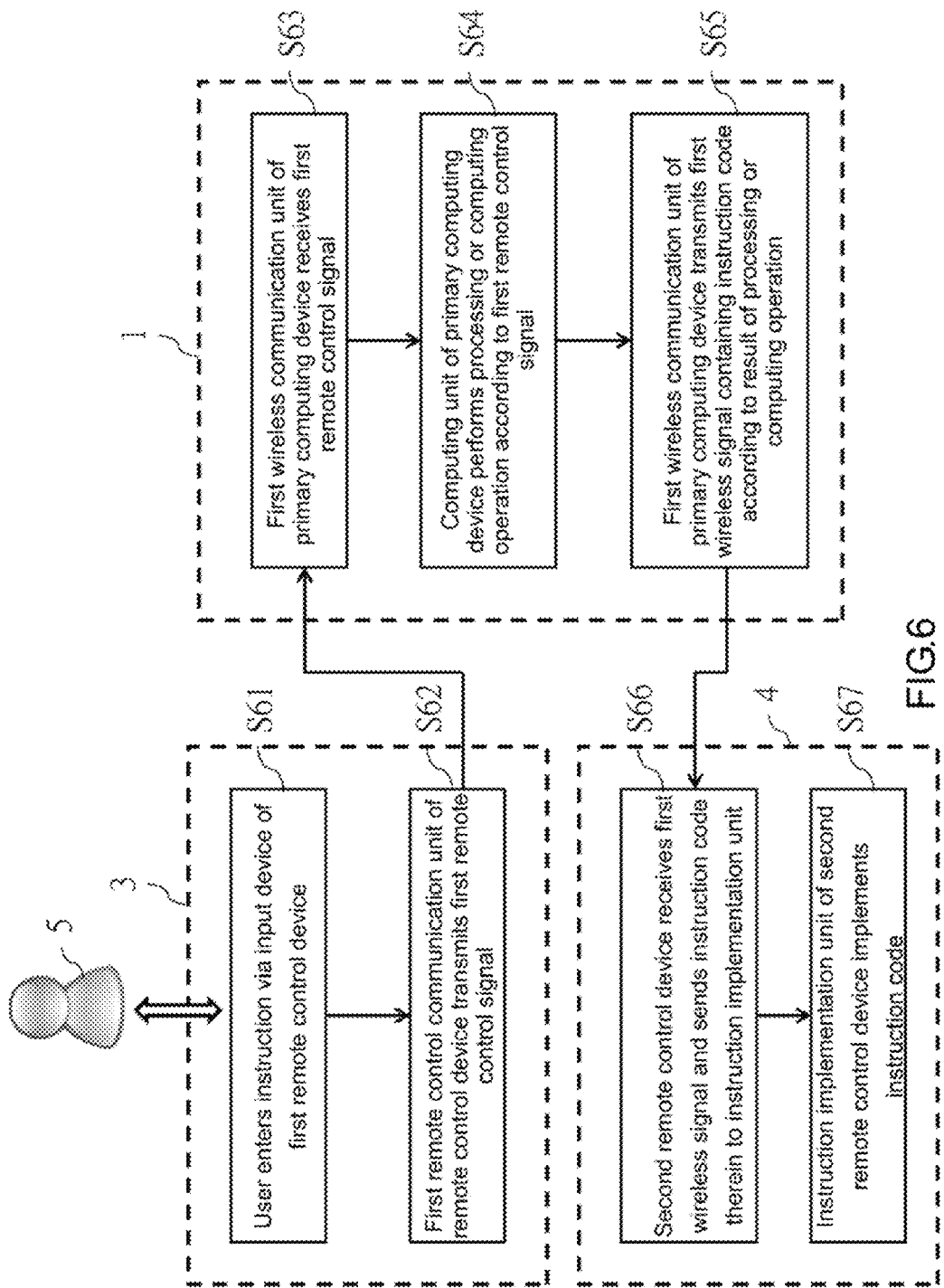
FIG. 6 is a flow chart illustrating the operation of the separate computing system according to the third embodiment of the present invention.

Referring to FIG. 6, there is shown a flow chart illustrating the operation of the separate computing system according to the third embodiment of the present invention. As shown in FIG. 6, steps S61~S62 are implemented on the first remote control device 3, steps S63~S65 are implemented on the primary computing device 1, and steps S66~S67 are implemented on the second remote control device 4. For the sake of better understanding of the present invention, the primary computing device 1 is exemplified by a smartphone, the first remote control device 3 is exemplified by a wireless keyboard, and the second remote control device 4 is exemplified by a projector. Similarly, the third embodiment described herein is to be deemed as illustrative, rather than restrictive, of the scope of the present invention. The first remote control device 3 can also be one of a keyboard, a mouse, a microphone, a camcorder, and a touchscreen, or a combination thereof. The second remote control device 4 can be a liquid crystal screen or a tablet computer. Furthermore, the flow chart in FIG. 6 omits, for example, the following similar operation processes depicted in FIGS. 2 and 4: the smartphone transmits externally a generated instruction code by means of the first wireless communication unit 16 after performing the processing operation or computing operation with the computing unit according to the user's instruction; after a second remote control communication unit 41 of the projector has received the instruction code, the microprocessor 42 determines the content of a piece of information and projects the content of the piece of information onto the screen according to the instruction code.

In step S61, the user 5 enters an instruction via a key (i.e., the input device 33) of a wireless keyboard (i.e., the first remote control device 3). For instance, as the screen of the smartphone is small, the user 5 can enter the instruction more easily with the wireless keyboard. Before the primary computing device 1 begins to communicate with all the remote control devices, the identity authentication unit 17 thereof must, in practice, perform the identity authentication procedure on all the remote control devices. Once the identity authentication procedure has been completed, both the first remote control device 3 and the second remote control device 4 have to be synchronized with the primary computing device 1 so that the user's input via the wireless keyboard (i.e., the first remote control device 3) and the display of information by the projector (i.e., the second remote control device 4) occur in synchrony with the related operation of the smartphone. In step S62, the first remote control communication unit 31 of the wireless keyboard transmits a first remote control signal to the first wireless communication unit 16 of the smartphone (i.e., the primary computing device 1). After the first wireless communication unit 16 of the smartphone has received the first remote control signal (step S63), the computing unit 12 of the smartphone performs the processing operation or computing operation according to the first remote control signal (step S64), such that the first wireless communication unit 16 of the smartphone transmits a first wireless signal containing an instruction code to the second remote control communication unit 41 of the projector (i.e., the second remote control device 4) according to the result of the processing operation or computing operation (step S65). In step S66, after receiving the first wireless signal, the second remote control communication unit 41 of the projector sends the instruction code in the first wireless signal to the microprocessor 42. Next, the microprocessor 42 controls a projection element (i.e., an instruction implementation unit 43) according to the instruction code so as to implement the content of the instruction code (step S67). Therefore, the input of information to the smartphone can be made with a keyboard, and the inputted information can be displayed by the projector which projects the information, thereby facilitating the input of information and providing an improved viewing experience.

In conclusion, the separate computing system of the present invention enables complex computing operations to be performed on a primary computing device, such as a smartphone, via wireless transmission, and thus a remote control device, such as a wristband, a pair of eyeglasses or a watch, requires either no processor at all or only a simple microprocessor for facilitating the display of content. Hence, the remote control device can not only fulfill the goals of minimized weight, low power consumption, reduced cost, and enhanced computing capability, but also apply the conception of the present invention to facilitate the input of information and improve the viewing experience.

The preferred embodiments described above are exemplary and are not intended to limit the scope of the present invention. Hence, any equivalent modification and variation made to the aforesaid embodiments without departing from the spirit and scope of the present invention shall fall within the scope of the appended claims.

What is claimed is:

1. A system with a separate computing unit, comprising:
   a primary computing device comprising a computing unit, a control interface unit via which a user enters an instruction and a first wireless communication unit, the computing unit performing the processing operation or the computing operation to generate an instruction code after receiving the instruction, the first wireless communication unit transmitting a first wireless signal containing the instruction code; and
   a remote control device comprising an instruction implementation unit, and a second wireless communication unit receiving the first wireless signal and sending the instruction code in the first wireless signal to the instruction implementation unit to implement the instruction code,
   wherein operation of the instruction implementation unit of the remote control device is controlled by the instruction code, and the instruction implementation unit does not have a capability of a processing operation or a computing operation; and
   wherein the second wireless communication unit only has one way communication capability of the receiving the first wireless signal.

2. The system with a separate computing unit of claim 1, wherein the control interface unit is selected from one of a touchscreen, a voice-controlled device, and a physical key.

3. The system with a separate computing unit of claim 1, wherein the first wireless communication unit is selected from one of a WiFi communication unit, an NFC communication unit, a RFID communication unit, a Bluetooth communication unit, a Zigbee communication unit, and an infrared communication unit.

4. The system with a separate computing unit of claim 1, wherein the second wireless communication unit is selected from one of a WiFi communication unit, an NFC communication unit, a RFID communication unit, a Bluetooth communication unit, a Zigbee communication unit, and an infrared communication unit.

5. The system with a separate computing unit of claim 1, wherein the instruction code is an uncoded control signal.

6. The system with a separate computing unit of claim 5, wherein a value of a register of the instruction implementation unit is changed according to the control signal so as to control the instruction implementation unit to perform a specific operation.

7. The system with a separate computing unit of claim 1, wherein the remote control device further has a microprocessor that processes the instruction code and controls the instruction implementation unit.

8. The system with a separate computing unit of claim 7, wherein the remote control device is a pair of eyeglasses equipped with a projection element via which an image is projected onto a lens, and a content of the image is determined after the microprocessor has processed the instruction code.

9. The system with a separate computing unit of claim 7, wherein the remote control device is a watch that displays a piece of information on a screen thereof, and a content of the piece of information is determined after the microprocessor has processed the instruction code.

10. The system with a separate computing unit of claim 7, wherein the instruction implementation unit of the remote control device is a screen that displays an information frame, and a content of the information frame is determined after the microprocessor has processed the instruction code.

11. The system with a separate computing unit of claim 1, wherein the primary computing device further comprises an identity authentication unit that performs an identity authentication procedure on the remote control device.

12. The system with a separate computing unit of claim 1, further comprising one or more other remote control devices synchronously controlled by the primary computing device through the first wireless signal.

* * * * *